United States Patent
Do

(10) Patent No.: US 11,501,865 B2
(45) Date of Patent: Nov. 15, 2022

(54) SYSTEMS AND METHODS FOR PROCESSING PRESCRIPTION AND MEDICAL DOCUMENTS

(71) Applicant: MedEssist Limited, Toronto (CA)

(72) Inventor: Michael Do, Toronto (CA)

(73) Assignee: MedEssist Limited, Toronto (CA)

( * ) Notice: Subject to any disclaimer, the term of this patent is extended or adjusted under 35 U.S.C. 154(b) by 389 days.

(21) Appl. No.: 16/870,432

(22) Filed: May 8, 2020

(65) Prior Publication Data

US 2020/0357499 A1   Nov. 12, 2020

Related U.S. Application Data

(60) Provisional application No. 62/846,314, filed on May 10, 2019.

(51) Int. Cl.
| | |
|---|---|
| *G16H 20/13* | (2018.01) |
| *G06V 30/413* | (2022.01) |
| *G07C 9/37* | (2020.01) |
| *G16H 40/20* | (2018.01) |

(52) U.S. Cl.
CPC .......... *G16H 20/13* (2018.01); *G06V 30/413* (2022.01); *G07C 9/37* (2020.01); *G16H 40/20* (2018.01)

(58) Field of Classification Search
CPC .............................. G16H 20/13; G06V 30/413
See application file for complete search history.

(56) References Cited

U.S. PATENT DOCUMENTS

| | | | |
|---|---|---|---|
| 8,032,397 B2 | 10/2011 | Lawless | |
| 2004/0162835 A1 | 8/2004 | Ghouri | |
| 2009/0048871 A1 | 2/2009 | Skomra | |
| 2009/0259493 A1 | 10/2009 | Venon et al. | |
| 2012/0101847 A1 | 4/2012 | Johnson et al. | |
| 2012/0173319 A1 | 7/2012 | Ferrara | |
| 2013/0096953 A1 | 4/2013 | Beverly et al. | |
| 2015/0371001 A1* | 12/2015 | Pinsonneault | G16H 20/10 705/2 |

OTHER PUBLICATIONS

Medisafe, "Medisafe Demonstrates Multi-Month Adherence Lift in Study by IMS Health", Oct. 29, 2015, 6 pages <https://www.prnewswire.com/news-releases/medisafe-demonstrates-multi-month-adherence-lift-in-study-by-ims-health-300168903.html>.

(Continued)

*Primary Examiner* — Daniell L Negron
(74) *Attorney, Agent, or Firm* — Bereskin & Parr LLP/S.E.N.C.R.L., s.r.l.; Tony Orsi

(57) ABSTRACT

Various embodiments are described herein for a system and method for determining a medical product dispensed by a pharmacy. The method involves operating a processor to: receive, from a computing device, image data depicting at least a portion of a prescription document issued by the pharmacy; extract, from the image data, a pharmacy identifier for identifying the pharmacy associated with issuing the prescription document; select, based on the pharmacy identifier, at least one parsing method for parsing prescription documents issued by the pharmacy identified by the pharmacy identifier; and apply the selected parsing method to the image data to determine a medical product identifier for identifying the medical product dispensed by the pharmacy.

20 Claims, 9 Drawing Sheets

(56) References Cited

OTHER PUBLICATIONS

Hinton, "2018 Updated: Smartphone, Tablet Use by Age", Creating Results, Mar. 27, 2018, 6 pages <https://creatingresults.com/2018/03/27/smartphone-tablet-use-age-gender-2018-update>.

Bulik, "Nonadherence costs pharma $600B-plus in annual sales: study", FiercePharma, Nov. 22, 2016, 3 pages <https://www.fiercepharma.com/marketing/non-adherence-costs-healthcare-system-patient-outcomes-and-pharma-bottom-line>.

Viswanathan et al., "Interventions to Improve Adherence to Self-administered Medications for Chronic Diseases in the United States: A Systematic Review", Annals of Internal Medicine, Dec. 4, 2012, 157(11): 785-795, W-285 to W-289.

Brown et al., "Medication Adherence: WHO Cares?", Mayo Clin Proc., Apr. 2011, 86(4): 304-314.

* cited by examiner

SYSTEMS AND METHODS FOR PROCESSING PRESCRIPTION AND MEDICAL DOCUMENTS

CROSS-REFERENCE TO RELATED APPLICATION

This application claims the benefit of U.S. Provisional Patent Application No. 62/846,314, filed May 10, 2019, and the entire contents of U.S. Provisional Patent Application No. 62/846,314 is hereby incorporated by reference.

FIELD

The various embodiments described herein generally relate to devices for processing prescriptions and systems for facilitating medical product and patient specific communications through prescription and medical document scanning.

BACKGROUND

Approximately 50% of patients do not take their medications as prescribed. Medication adherence is defined as the proper usage of a medication as intended by the prescriber. This includes taking the medication at the right time, frequency, dosage, as well as in the correct manner and duration. Medication non-adherence is a tremendous burden for patients, pharmacies, and the pharmaceutical industry alike. In the US, 125,000 deaths and 10% of hospitalizations each year are attributed to medication non-adherence. Medication non-adherence costs the pharmaceutical industry $637 billion USD globally.

SUMMARY OF VARIOUS EMBODIMENTS

In one broad aspect, in at least one embodiment described herein, there is provided a computer implemented method for determining a medical product dispensed by a pharmacy. The method involves operating a processor to: receive, from a computing device, an image data depicting at least a portion of a prescription document issued by the pharmacy; extract, from the image data, a pharmacy identifier for identifying the pharmacy associated with issuing the prescription document; select, based on the pharmacy identifier, at least one parsing method for parsing prescription documents issued by the pharmacy identified by the pharmacy identifier; and apply the selected parsing method to the image data to determine a medical product identifier for identifying the medical product dispensed by the pharmacy.

In at least one embodiment, applying the selected parsing method to the image data can include: determining, based on the pharmacy identifier, at least one format associated with the medical product identifier; determining, based on the pharmacy identifier, at least one location in the image data associated with the medical product identifier; extracting, from the image data, at the at least one determined location, image data associated with the medical product identifier; and processing the associated image data, based on the at least one format, to determine the medical product identifier.

In at least one embodiment, processing the associated image data can include removing at least some of the associated image data based on the at least one format.

In at least one embodiment, extracting the pharmacy identifier can include extracting, from the image data, a telephone number associated with the pharmacy.

In at least one embodiment, extracting the pharmacy identifier can include extracting text data from the image data, and extracting the pharmacy identifier from the text data. Applying the selected parsing method to the image data can include applying the selected parsing method to the text data to determine the medical product identifier.

In at least one embodiment, the medical product identifier can include at least one of: a National Drug Code (NDC), a Drug Identification Number (DIN), and Natural Product Number (NPN).

In at least one embodiment, the method can further involve operating the processor to: apply the selected parsing method to the image data to determine a prescription identifier for identifying a prescription associated with the prescription document.

In at least one embodiment, the prescription identifier can include a prescription (Rx) number.

In at least one embodiment, the method can further involve operating the processor to: determine, based on the medical product identifier, at least one instruction for administering the medical product associated with the medical product identifier; and transmit the at least one instruction to the computing device.

In at least one embodiment, the method can further involve operating the processor to: determine, based on the medical product identifier, a plurality of other computing devices associated with the drug associated with the medical product identifier; transmit the at least one instruction to the computing device and the plurality of other computing devices.

In at least one embodiment, receipt of the at least one instruction can cause a processor of the computing device to: generate a notification for alerting a user to administer the medical product.

In at least one embodiment, transmitting the at least one instruction can include transmitting at least one of: a video file, an audio file, and a text file to the computing device.

In at least one embodiment, the method can further involve operating the processor to: receive, from the computing device, a user request for refilling a prescription associated with the prescription document; locate, based on the pharmacy identifier, a pharmacy server associated with the pharmacy associated with issuing the prescription document; generate a server request for refilling the prescription; and transmit the server request for refilling the prescription to the pharmacy server, the server request including the medical product identifier.

In at least one embodiment, the method can further involve operating the processor to: transmit a request for at least one physiological measurement of a user associated with administration of the medical product to the computing device; receive, from the computing device, the at least one physiological measurement; and store, in a memory, the at least one physiological measurement with the medical product identifier.

In another aspect, in at least one embodiment described herein, there is provided a system for determining a medical product dispensed by a pharmacy. The system includes a memory and a processor. The memory can store a plurality of parsing methods, each parsing method for parsing prescription documents issued by a particular pharmacy. The processor is operable to: receive, from a computing device, image data depicting at least a portion of a prescription document issued by the pharmacy; extract, from the image data, a pharmacy identifier for identifying the pharmacy associated with issuing the prescription document; select, based on the pharmacy identifier, at least one parsing method stored in the memory for parsing prescription documents issued by the pharmacy identified by the pharmacy identifier; and apply the selected parsing method to the image data to determine a medical product identifier for identifying the medical product dispensed by the pharmacy.

In at least one embodiment, applying the selected parsing method to the image data can include: determining, based on the pharmacy identifier, at least one format associated with the medical product identifier; determining, based on the pharmacy identifier, at least one location in the image data associated with the medical product identifier; extracting, from the image data, at the at least one determined location, image data associated with the medical product identifier; and processing the associated image data, based on the at least one format, to determine the medical product identifier.

In at least one embodiment, processing the associated image data to determine the medical product identifier can include removing at least some of the associated image data based on the at least one format.

In at least one embodiment, extracting the pharmacy identifier can include extracting, from the image data, a telephone number associated with the pharmacy.

In at least one embodiment, extracting the pharmacy identifier can include: extracting text data from the image data, and extracting the pharmacy identifier from the text data. Applying the selected parsing method to the image data can include: applying the selected parsing method to the text data to determine the medical product identifier.

In at least one embodiment, the medical product identifier can include at least one of: a National Drug Code (NDC), a Drug Identification Number (DIN), and Natural Product Number (NPN).

In at least one embodiment, the processor can be further operable to: apply the selected parsing method to the image data to determine a prescription identifier for identifying the prescription associated with the prescription document.

In at least one embodiment, the prescription identifier can include a prescription (Rx) number.

In at least one embodiment, the processor can be further operable to: determine, based on the medical product identifier, at least one instruction for administering the medical product associated with the medical product identifier; and transmit the at least one instruction to the computing device.

In at least one embodiment, the processor can be further operable to: determine, based on the medical product identifier, a plurality of other computing devices associated with the medical product associated with the medical product identifier; transmit the at least one instruction to the computing device and the plurality of other computing devices.

In at least one embodiment, receipt of the at least one instruction can cause a processor of the computing device to: generate a notification for alerting a user to administer the medical product.

In at least one embodiment, transmitting the at least one instruction can include transmitting at least one of: a video file, an audio file, and a text file to the computing device.

In at least one embodiment, the processor can be further operable to: receive, from the computing device, a user request for refilling a prescription associated with the prescription document; locate, based on the pharmacy identifier, a pharmacy server associated with the pharmacy associated with issuing the prescription document; generate a server request for refilling the prescription; and transmit the server request for refilling the prescription to the pharmacy server, the server request including the medical product identifier.

In at least one embodiment, the processor can be further operable to: transmit a request for at least one physiological measurement of a user associated with administration of the medical product to the computing device; receive, from the computing device, the at least one physiological measurement; and store, in the memory, the at least one physiological measurement with the medical product identifier.

In another aspect, in at least one embodiment described herein, there is provided a computing device for determining a medical product dispensed by a pharmacy. The computing device includes an interface for communication and a processor that is operatively coupled to the interface, the processor being configured to: receive an image data depicting at least a portion of a prescription document issued by the pharmacy; extract, from the image data, a pharmacy identifier for identifying the pharmacy associated with issuing the prescription document; select, based on the pharmacy identifier, at least one parsing method for parsing prescription documents issued by the pharmacy identified by the pharmacy identifier; and apply the selected parsing method to the image data to determine a medical product identifier for identifying the medical product dispensed by the pharmacy.

In at least one embodiment, the processor is configured to apply the selected parsing method to the image data includes: determine, based on the pharmacy identifier, at least one format associated with the medical product identifier; determine, based on the pharmacy identifier, at least one location in the image data associated with the medical product identifier; extract, from the image data, at the at least one determined location, image data associated with the medical product identifier; and process the associated image data, based on the at least one format, to determine the medical product identifier.

In at least one embodiment, the processor is configured to process the associated image data includes removing at least some of the associated image data based on the at least one format.

In at least one embodiment, the processor is configured to extract the pharmacy identifier by extracting, from the image data, a telephone number associated with the pharmacy.

In at least one embodiment, the processor is configured to extract the pharmacy identifier by: extracting text data from the image data, and extracting the pharmacy identifier from the text data; and applying the selected parsing method to the image data comprises: applying the selected parsing method to the text data to determine the medical product identifier.

In at least one embodiment, the medical product identifier includes at least one of: a National Drug Code (NDC), a Drug Identification Number (DIN), and Natural Product Number (NPN).

In at least one embodiment, the processor is further configured to apply the selected parsing method to the image data to determine a prescription identifier for identifying a prescription associated with the prescription document.

In at least one embodiment, the prescription identifier includes a prescription (Rx) number.

In at least one embodiment, the processor is further configured to receive at least one instruction for administering the medical product associated with the medical product identifier.

In at least one embodiment, receipt of the at least one instruction causes the processor of the computing device to generate a notification for alerting a user to administer the medical product.

In at least one embodiment, receiving the at least one instruction comprises receiving at least one of: a video file, an audio file, and a text file.

In at least one embodiment, the processor is configured to perform at least one of: displaying a video from the video file to the user, providing a sound output for audio in the audio file to the user and display text from the text file to the user.

In at least one embodiment, the processor is further configured to generate and transmit a user request for refilling a prescription associated with the prescription document.

In at least one embodiment, the processor is further configured to: receive a request for at least one physiological measurement of a user associated with administration of the medical product; and transmit the at least one physiological measurement.

Other features and advantages of the present application will become apparent from the following detailed description taken together with the accompanying drawings. It should be understood, however, that the detailed description and the specific examples, while indicating preferred embodiments of the application, are given by way of illustration only, since changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
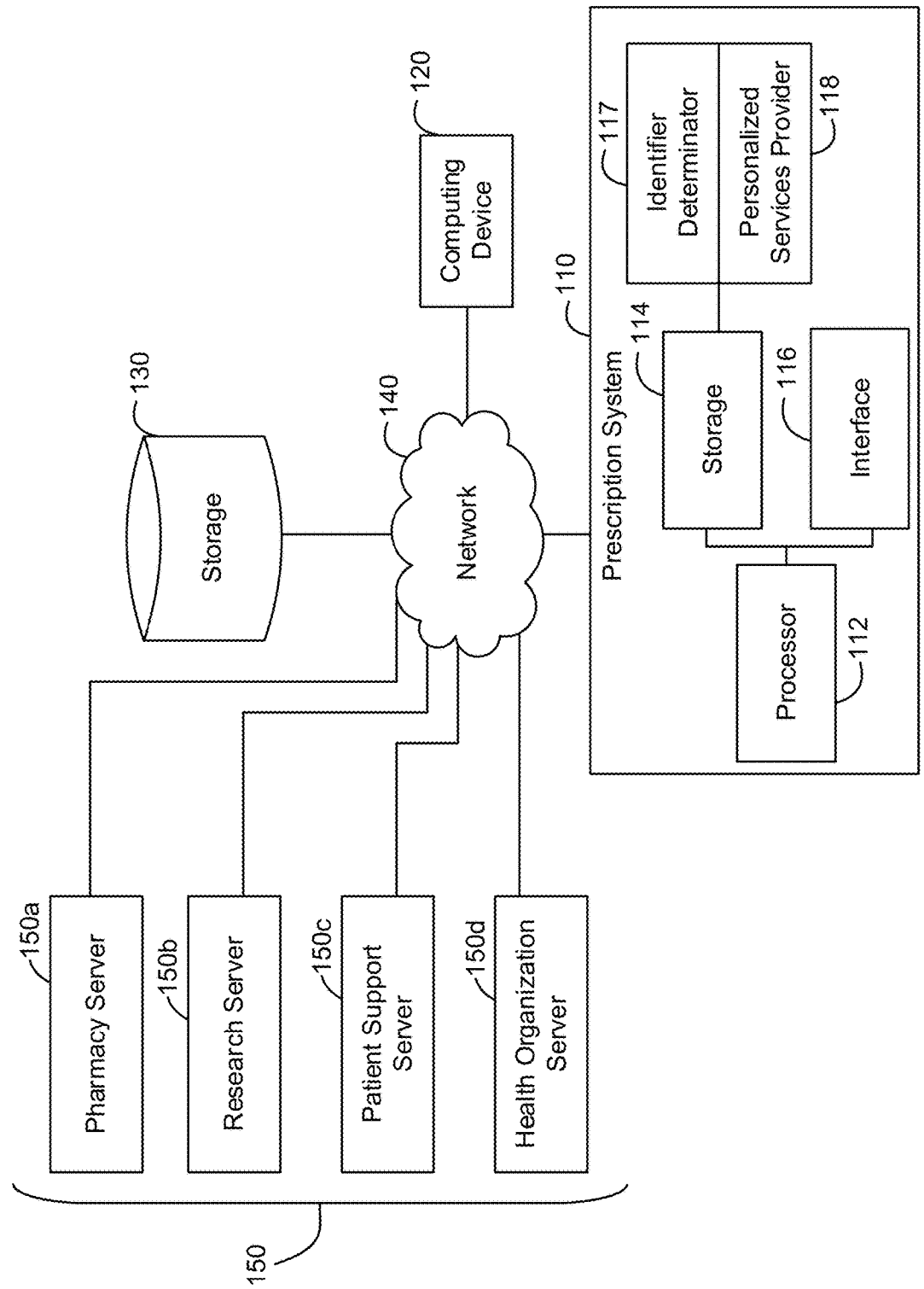
FIG. 1 is a block diagram of an example embodiment of a prescription system that can automatically process prescriptions for facilitating medication and patient specific communications through prescription document scanning components and various other components in accordance with the teachings herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have an electrical connotation. For example, as used herein, the terms coupled or coupling can indicate that two elements or devices can be directly connected to one another or connected to one another through one or more intermediate elements or devices via an electrical signal, electrical connection, or communication pathway depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

The example embodiments of the devices, systems and methods described in accordance with the teachings herein may be implemented in hardware or software, or a combination of both. For example, the embodiments described herein may be implemented, at least in part, by using one or more computer programs, executing on one or more programmable on programmable devices comprising at least one processing element and at least one data storage element (including volatile memory or non-volatile memory or other data storage elements or a combination thereof), and at least one communication interface. For example and without limitation, the programmable devices (referred to below as computing devices or user devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, a communication interface is included which may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information may be applied to one or more output devices. Each program may be implemented in a high level procedural or object oriented programming and/or scripting language, or both, to communicate with a computer system. However, the programs may be implemented in assembly or machine language, if desired. In any case, the language may be a compiled or interpreted language.

Each such computer program may be stored on a storage media or a device (e.g. ROM, magnetic disk, optical disc, a USB key) that is readable by a computing device, for configuring and operating the computing device to operate as a special purpose programmable computer when the storage media or device is read by the computing device to perform the procedures described herein. Embodiments of the system may also be considered to be implemented as a non-transitory computer-readable storage medium that stores various computer programs, that when executed by a computing device, causes the computing device to operate in a specific and predefined manner to perform at least one of the functions described in accordance with the teachings herein.

Furthermore, the system, processes and methods of the described embodiments are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage media as well as transitory forms such as, but not limited to, wireline transmissions, satellite transmissions, internet transmission or downloads, digital and analog signals, and the like. The computer useable instructions may also be in various forms, including compiled and non-compiled code.

The number of seniors using smartphones has nearly quadrupled between 2012 and 2017 in the US. 46% of Americans ages 65+ and 75% of those ages 50-64 now own a smartphone. Based on this mobile device use, medication reminder mobile applications have been developed for use with mobile devices. While these medication reminder mobile applications have shown an increase in adherence by 8.4-19.5%, their popularity may be limited by a high barrier of entry, simplistic functionality and requiring users to enter information, which may be difficult for elderly people.

For example, some mobile apps (i.e. applications) require patients to type in medication names, doses, directions of use, and other information into the app. Many patients may be discouraged to use an app that requires self-input, as it may seem complicated and error-prone. Other mobile apps provide patients with remote access to their pharmacy profile. However, patients are required to register and set up an account, which can be inconvenient and complex for some patients. The pharmacy profile that patients are given access to may also provide too much information in a format that is not patient friendly. There are also security concerns with having patient records available online. Furthermore, some mobile apps are limited to providing notifications at times set by the patient. In these cases, all medication entries are handled by the mobile apps in the same way and the patient experience is identical, regardless of their medication therapy. Without medication specific content or communication, patients may become uninterested in the experience and may not learn how to properly take their medication or perform other behaviors that may be beneficial for their medical conditions for which they are taking medication.

In accordance with the teachings herein, there is provided at least one embodiment that generally relates to devices, systems and methods of processing prescriptions for facilitating medication and patient specific communications through prescription document scanning. For example, the prescription system disclosed herein can provide patients with medical product, prescription, and pharmacy specific functionality. The prescription system can, for example, determine a medical product, pharmacy, and/or prescription identifier (such as a National Drug Code (NDC), a pharmacy phone number, or prescription (Rx) number), based on image data of a prescription document. Accordingly, the patient can avoid manual entry of information, resulting in greater ease of use and fewer errors. Since the medical products, pharmacies, and/or prescriptions are identified using identifiers, use of personal information can be avoided, preserving privacy and security.

The prescription system disclosed herein can create a unique patient experience that is specific to their medical product, pharmacy, and/or prescription. The prescription system can guide patients through every dose of their treatment and can deliver medical product specific communications from a variety of resources. The prescription system may address medical product non-adherence one or more ways such as, but not limited to, by reminding patients of dosing times, teaching patients how to use their medications, increasing health literacy, connecting patients to support programs, monitoring for side effects, monitoring medical product efficacy, and making it more convenient to order medical products.

It should be noted that the term "prescription document" as used herein may refer to a document that includes various medical information such as, but not limited to, a prescription, a prescription receipt, a label attached to a medication container, a medical laboratory record, a medication information handout, a medical record, a medication record, or a medication list. In some embodiments, a prescription document may include a list of multiple medications.

It should be noted that the term "medical product" as used herein may refer to a drug, a medication, or any other product that may be dispensed from a pharmacy. For example a medical product may include, but is not limited to, a supplement, a food product, a support product, a diabetes test strip, a vitamin, a diagnostic device, or a medical device.

It should be noted that the term "pharmacy" as used herein may refer to any medical office, or any other establishment for dispensing medical products, such as, but not limited to, a pharmacy, medical clinic, medical office, hospital, nursing home, surgical center, dental clinic, etc. A pharmacy may issue a prescription document for a medical product.

Referring now to FIG. 1, shown therein is a block diagram of an example embodiment of a prescription system 110 that can automatically process prescriptions for facilitating medical product and patient specific communications through prescription document scanning components and various other components in accordance with the teachings herein. The prescription system 110 includes a processor 112, a storage component 114, and an interface component 116. As shown in FIG. 1, the prescription system 110 can be in communication with an external storage component 130 and a computing device 120 via a network 140. The prescription system 110 can also be in communication with external servers 150, such as, but not limited to, pharmacy server 150a, research server 150b, patient support server 150c, and health organization server 150d via network 140. Although the prescription system 110 is shown as one component in FIG. 1, in some embodiments, the prescription system 110 can be provided with one or more components distributed over a wide geographic area and connected via the network 140.

The processor 112 may be any suitable processor, controller or digital signal processor that provides sufficient processing power depending on the configuration, purposes and requirements of the prescription system 110. In some embodiments, the processor 112 may be replaced with two or more processors with each processor being configured to perform different dedicated tasks. The processor 112 controls the operation of the prescription system 110. For example, the processor 112 can process image data depicting at least a portion of a prescription document that includes medication information.

The interface component 116 may be any interface that enables the prescription system 110 to communicate with other devices and systems. In some embodiments, the interface component 116 can include at least one of a serial port, a parallel port or a USB port. The interface component 116 may also include at least one of an Internet, Local Area Network (LAN), Ethernet, Firewire, modem or digital subscriber line connection. Various combinations of these elements may be incorporated within the interface component 116.

For example, the interface component 116 may receive input from various input devices, such as a mouse, a keyboard, a touch screen, a thumbwheel, a track-pad, a track-ball, a card-reader, voice recognition software and the like depending on the requirements and implementation of the prescription system 110. The interface component 116 may also be used to provide output data to various output devices such as at least one of a display, a vibrator, a speaker and a printer. The interface component 116 may also be used to provide data and/or receives data via a graphical user interface that is shown on a display for a user to interact with.

The storage component 114 can include RAM, ROM, one or more hard drives, one or more flash drives or some other suitable data storage elements such as disk drives, etc. For example, the storage component 114 can include a memory on which one or more databases or file system(s) are stored. The database(s) can, but is not limited to, store information related to medical products, pharmacies, and prescriptions processed via the prescription system 110. For example, the storage component 114 can store pharmacy data, such as, but not limited to at least one of, pharmacy identifiers, names, phone numbers, fax numbers, addresses, hours, available services (e.g., flu shot availability, delivery, etc.), prescription formats, parsing methods, and images or videos (e.g., logos or storefront images of pharmacies, instructional or counseling videos for medications, images of medications, packaging, or medical devices, etc.). The storage component 114 can also store medical product data, such as, but not limited to, at least one of medical product identifiers, prescriptions identifiers, brand names, generic names, common doses, units, common directions, common instructions, custom interfaces, images, and videos. It will be appreciated that the storage component 114 may store links, references, or locations to data, rather than the data itself. The storage component 114 can also include software code for implementing an identifier determinator 117 and a personalized services provider 118. As will be described in further detail below, the identifier determinator 117 can determine medical product identifiers, pharmacy identifiers, and/or prescription identifiers and the personalized services provider 118 can provide various personalized or customized services, experiences or functionalities based on the medical product identifiers, pharmacy identifiers, and/or prescription identifiers.

Similar to the storage component 114, the external storage component 130 can include RAM, ROM, one or more hard drives, one or more flash drives or some other suitable data storage elements such as disk drives, etc. The external storage component 130 can include a memory on which one or more databases or file system(s) are stored. Although only one external storage component 130 is shown, there may be multiple external storage components 130 distributed over a wide geographic area and connected via the network 140.

The external storage component 130 can be accessed by the prescription system 110 via the network 140. The external storage component 130 can act as a back-up storage component to the storage component 114 and/or store at least some of the data related to the medical products, pharmacies, and/or and prescriptions processed via the prescription system 110. In some embodiments, the external storage component 130 can store data that is not as frequently used by the prescription system 110, or larger size data. It will be appreciated that the external storage component 130 may additionally store any of the data discussed above with respect to storage component 114. Alternatively, at least some of this data may be stored only on the external storage component 130.

In alternative embodiments, the prescription system 110 may comprise other components that are not shown in FIG. 1 as is known by those skilled in the art. The processor 112, the storage component 114, and the interface component 116 are generally implemented using a combination of software and hardware.

The computing device 120 may be any networked device operable to connect to the network 140. A networked device is a device capable of communicating with other devices through a network such as the network 140. A network device may couple to the network 140 through a wired or wireless connection.

Although only one computing device 120 is shown in FIG. 1, there may be multiple computing devices 120 in communication with the prescription system 110 via the network 140. The computing devices 120 can be distributed over a wide geographic area. For example, users in separate cities, provinces, states or countries can use a computing device 120 to access the prescription system 110 to obtain medical product administration instructions.

The computing devices 120 may include at least a processor and memory, and may be an electronic tablet device, a personal computer, workstation, a server, a portable computer, a mobile device, a personal digital assistant, a laptop, a smart phone, a WAP phone, an interactive television, video display terminals, gaming consoles, a wearable, a tablet, and portable electronic devices or any combination of these. In some embodiments, the computing device 120 may be a laptop or a smartphone device equipped with a network adapter for connecting to the Internet.

Similar to the computing devices 120, the external servers 150 may be any networked device operable to connect to the network 140. The external servers 150 may include at least one processor and memory. The external servers 150 can be distributed over a wide geographic area. As shown in FIG. 1, external servers 150 can include a pharmacy server 150a, a research server 150b, a patient support server 150c and a health organization server 150d. For example, a pharmacy can use pharmacy server 150 to transfer prescription format information to the prescription system 110 via the network 140. In another example, a pharmacy can use pharmacy server 150a to transmit a notification to prescription system 110 or computing device 120, indicating that a patient's medication order is ready. In some embodiments, at least one of the servers 150a to 150d may be replaced with one or more computing devices each running a client application that provides similar functionality. It will be appreciated that there can be any number and/or type of external servers 150 in communication with prescription system 110.

Figure 2:
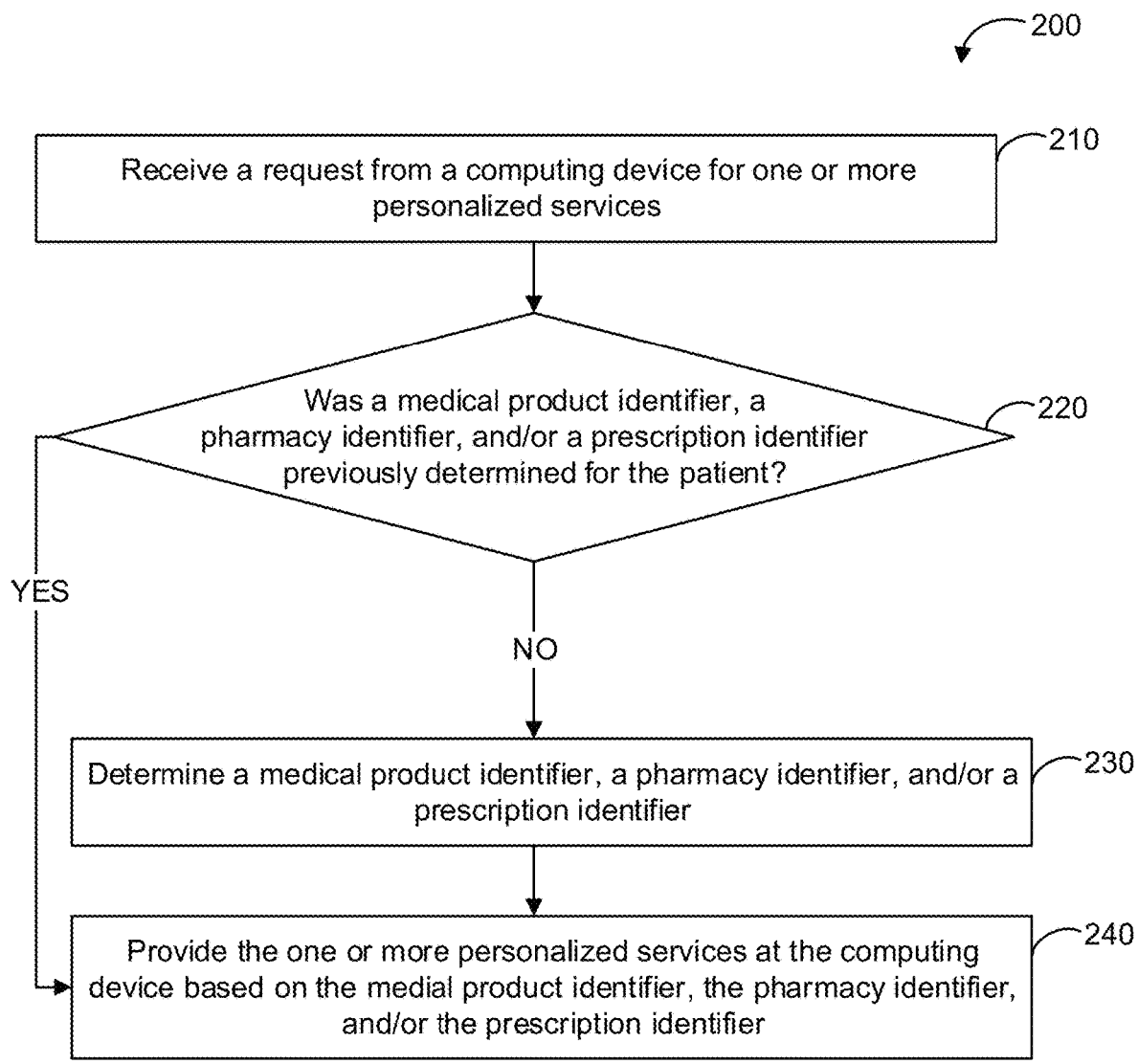
FIG. 2 is a flowchart of an example embodiment of a method of for automatically processing prescriptions for facilitating medication and patient specific communications in accordance with the teachings herein.
Figure 3:
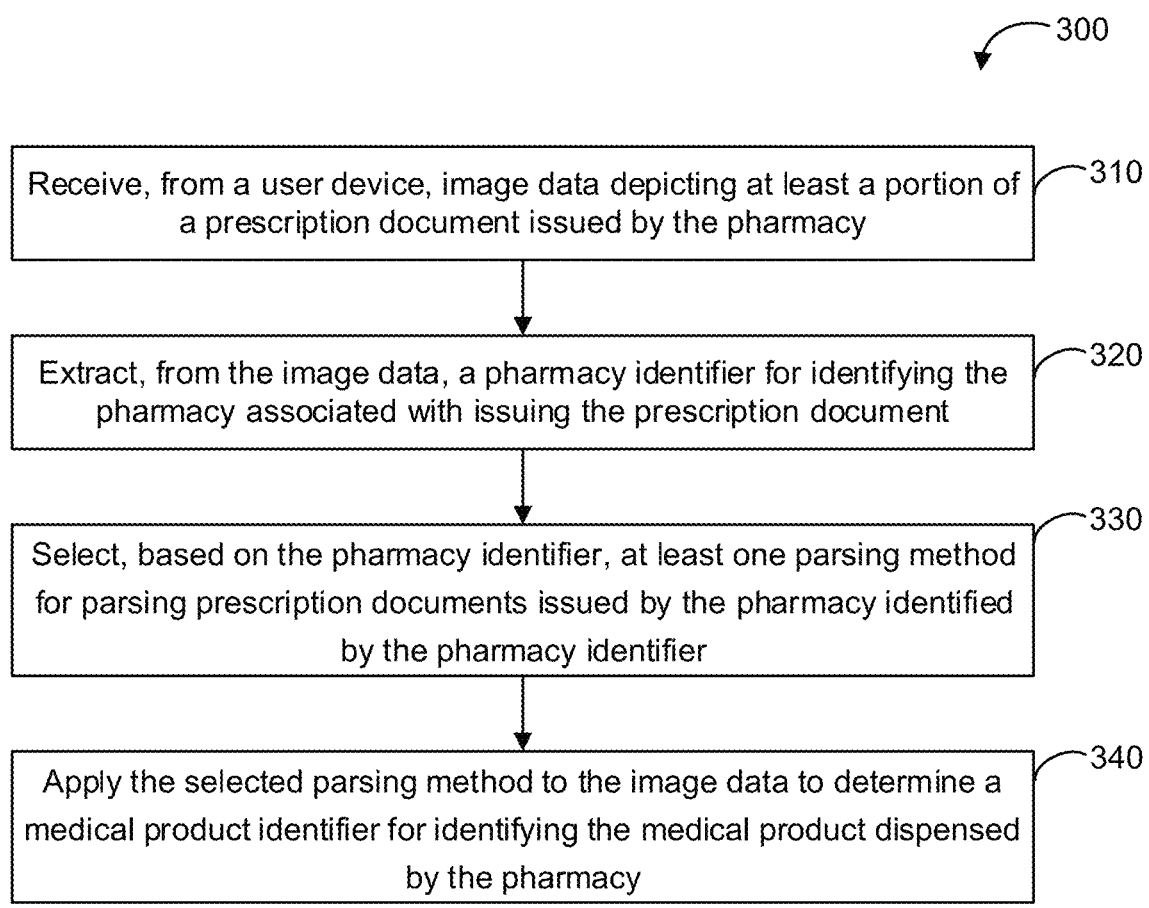
FIG. 3 is a flowchart of an example embodiment of a method for automatically obtaining medical product information from a prescription document in accordance with the teachings herein.
Figure 5:
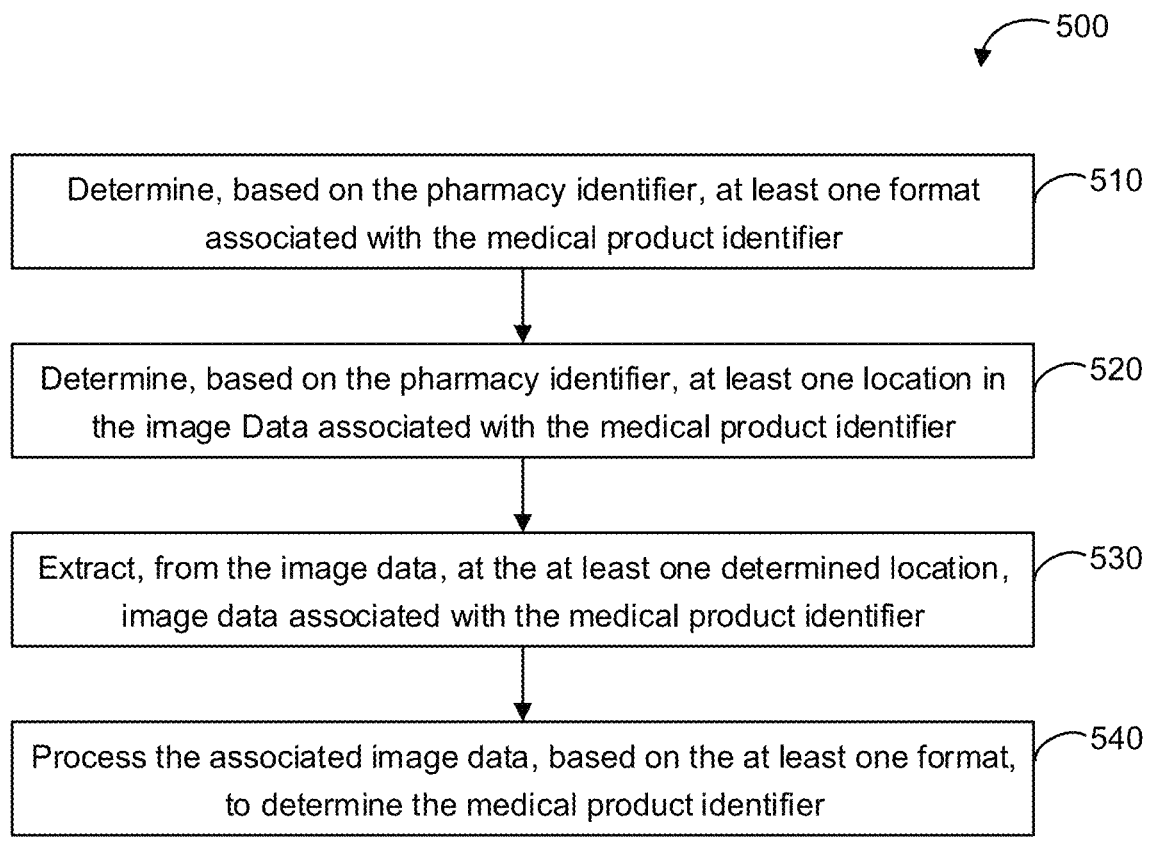
FIG. 5 is a flowchart of an example embodiment of a method of automatically obtaining medical product information from a prescription document in accordance with the teachings herein.

Reference is now made to FIGS. 2, 3, and 5, which show flowcharts of example embodiments of operating the prescription system 110 and some of the other components shown in FIG. 1. It should be noted that although some of the acts of the methods are described as being implemented on the prescription system 110, some or all of the acts may be implemented on the computing device 120.

Referring now to FIG. 2, shown therein is a flowchart of an example embodiment of a method 200 for automatically processing prescriptions for facilitating medical product and patient specific communications in accordance with the teachings herein. The method 200 can be implemented using the prescription system 110 and some of the other components shown in FIG. 1.

At act 210, the prescription system 110 receives a request from a computing device 120 for one or more personalized services. Various personalized services can be requested. For example, a user or patient using a computing device 120 can perform at least one of requesting information regarding a particular medical product, registering for a particular patient support program, registering to participate in a particular research study, requesting a refill of a particular prescription, requesting to transmit a side effect report regarding a particular medical product, register to receive news or information for a particular medical product, and request to transmit physiological measurements related to use of a particular medical product. The personalized service may be customized depending on at least one of a medical product, a pharmacy, or a prescription associated with the patient.

At act 220, the prescription system 110 determines whether a medical product identifier, a pharmacy identifier, or a prescription identifier was previously determined for the patient. If so, the prescription system can proceed to act 240. For example, in some cases, the prescription system 110 may have previously stored a medical product identifier, a pharmacy identifier, or a prescription identifier associated with the patient. If not, the prescription system 110 can proceed to act 230 and determine a medical product identifier, a pharmacy identifier or a prescription identifier.

At act 230, the prescription system 110 determines a medical product identifier, a pharmacy identifier, and/or a prescription identifier. In at least one embodiment, the prescription system 110 can determine the medical product identifier, the pharmacy identifier, and/or the prescription identifier based on image data depicting at least a portion of a prescription document. An example of a method for performing act 230 will be described in further detail below with respect to FIG. 3 and method 300.

At act 240, the prescription system 110 provides the one or more personalized services at the computing device 120 based on the medical product identifier, the pharmacy identifier, and/or the prescription identifier. Examples of personalized services that can be provided by the prescription system 110 will be discussed in further detail below with respect to FIGS. 7A to 7E.

Referring now to FIG. 3, shown therein is a flowchart of an example embodiment of a method 300 for automatically obtaining medical product information from a prescription document using the prescription system 110 in accordance with the teachings herein. The method 300 is an example method for determining a medical product identifier and may be implemented as act 230 of method 200 shown in FIG. 2. To illustrate the method 300, reference will also be made to FIGS. 4A, 4B, 6A, and 6B At act 310, the prescription system 110 receives, from a computing device 120, image data depicting at least a portion of a prescription document issued by the pharmacy. For example, a patient may use the computing device 120 to take a photo of at least a portion of a prescription document and transmit image data of the portion of the prescription document to the prescription system 110. It will be appreciated that in some embodiments, the image data may not be stored at the computing device 120 or the prescription system 110. For example, the prescription system 110 or computing device 120 may receive a live feed (i.e. stream) of image data and may perform various processing (as will be described below) on the live feed. Accordingly, the prescription system 110 may perform acts 310, 320, 330, and 340 repeatedly for a plurality of images in the live feed of image data.

Figure 6B:
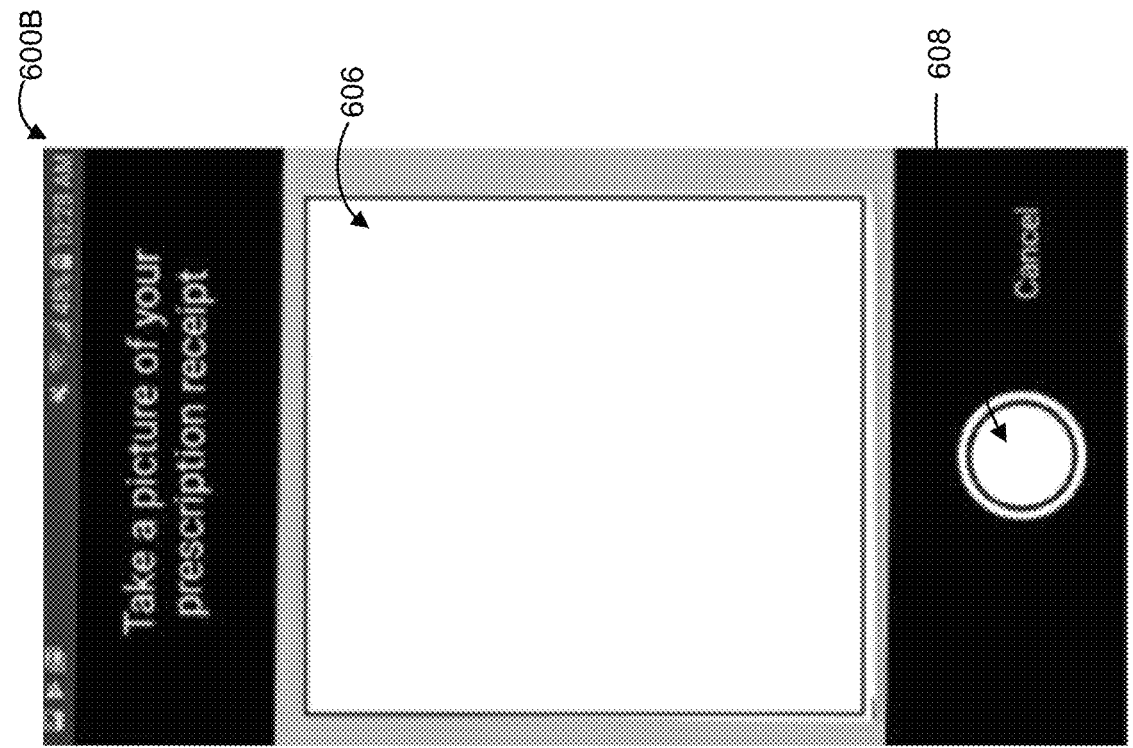
FIGS. 6A and 6B are illustrations of example embodiments of user interfaces that can be used to facilitate the operation of the prescription system disclosed herein.
Figure 6A:
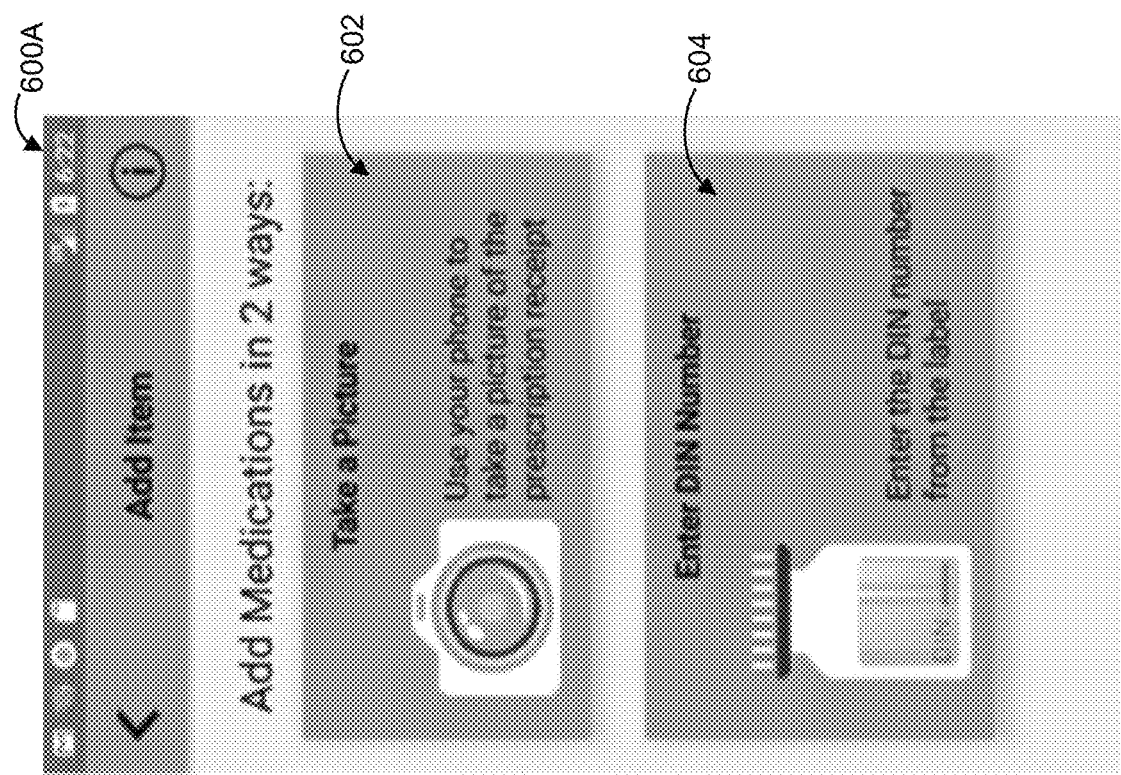

FIGS. 6A and 6B show example embodiments of user interfaces 600A and 600B for capturing image data of a prescription document using the computing device 120. Using interface 600A, a patient can activate button 602 in order to access an image preview and capture interface 600B. Image preview and capture interface 600B includes a preview window 606 and a capture button 608. A patient can preview the image of a prescription document to be captured using preview window 606 and acquire image data of the prescription document by activating the capture button 608. The image data can then be transmitted from the computing device 120 to the prescription system 110. However, as will be described below, in some cases, the patient may choose to not take a photo and can instead manually enter an identifier by selecting button 604.

Figure 4A:
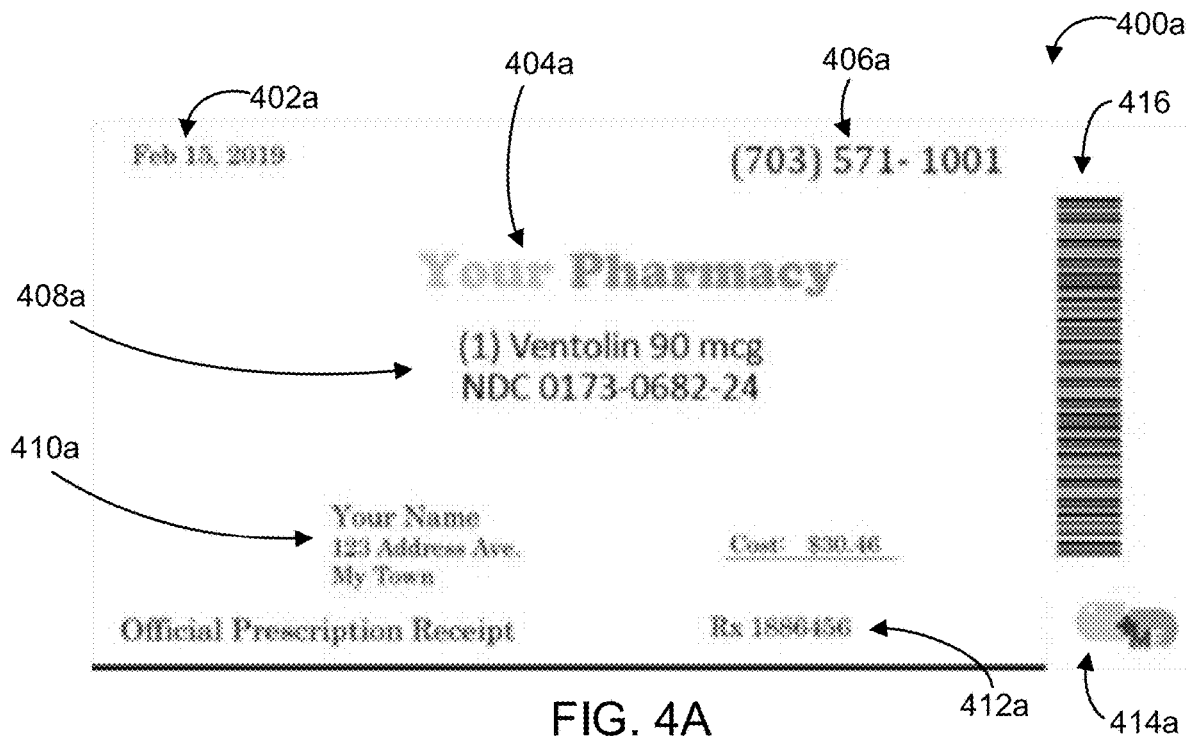
FIGS. 4A and 4B are illustrations of example prescription documents, which may be processed by the prescription system disclosed herein.
Figure 4B:
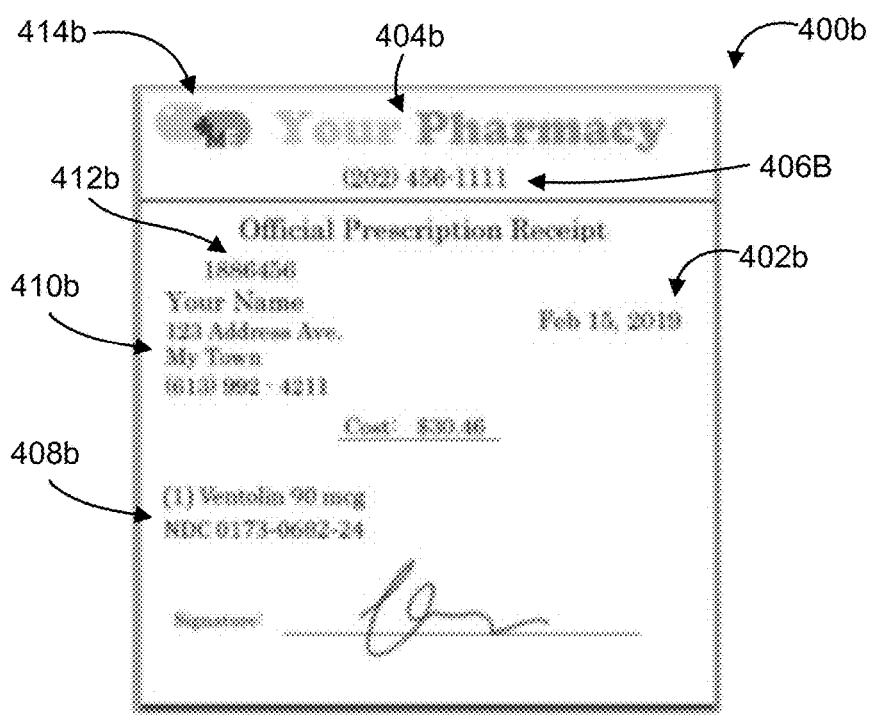

A prescription document can include various information that can be used by the prescription system 110. FIGS. 4A and 4B show two example prescription documents 400A and 400B. Prescription documents 400A and 400B include prescription dates 402a, 402b; pharmacy names 404a, 404b; pharmacy phone numbers 406a, 406b; medical product information 408a, 408b; patient information 410a, 410b; prescription number 412a, 412b; and pharmacy logo 414a, 414b, respectively. Prescription document 400A has a different format than prescription document 400B. That is, the information presented in prescription document 400A is presented in different positions, using different fonts, and using different sizes, relative to prescription document 400B. Moreover, the size of prescription document 400A is different than prescription document 400B. Furthermore, prescription document 400A includes information which is not included in prescription document 400B, such as barcode 416.

Prescription documents 400A and 400B are shown for illustrative purposes. It will be appreciated that a prescription document may not include all of the information shown in FIGS. 4A and 4B. Furthermore, a prescription document may include other information not shown in FIGS. 4A and 4B. Moreover, a prescription document may have a format different than that shown in FIGS. 4A and 4B.

Referring back to FIG. 3, at act 320, the prescription system 110 extracts, from the image data, a pharmacy identifier. The pharmacy identifier can be any identifier for identifying the pharmacy associated with issuing the prescription document. For example, in some cases, the pharmacy identifier may include a telephone number associated with the pharmacy, such as the telephone number 406a from the prescription document 400a. In another example, the pharmacy identifier may include a name associated with the pharmacy, such as the pharmacy name 404a from the prescription document 400a.

In at least one embodiment, the prescription system 110 can extract text data from the acquired image data and extract the pharmacy identifier from the text data. For example, prescription system 110 may use an optical character recognition (OCR) method to extract text data from the acquired image data.

In at least one embodiment, the prescription system 110 can compare the extracted text data to predetermined pharmacy data to determine the pharmacy identifier. For example, the prescription system 110 may compare the extracted text data to data that is associated with particular pharmacies. Table 1 illustrates an example of pharmacy data which can be accessed by the prescription system 110. The pharmacy data can be stored, for example, at storage 114 and/or storage 130.

TABLE 1

Example Pharmacy Data

| Pharmacy Phone | (202) 456-1111 | (703) 571-1001 |
| Pharmacy Name | Your Pharmacy | Bob's Pharmacy |
| Pharmacy Fax | (202) 456-1311 | (703) 571-1343 |
| Pharmacy Barcode | ||| || || | | |||| | ||| | |
| Pharmacy Logo | Logo A | Logo B |
| Prescription Document Format Type | Type A | Type B |

For example, the extracted text data may include one or more phone numbers, such as the phone numbers 406b and 406b displayed in the pharmacy receipt 400b. The prescription system 110 can compare the phone numbers 406b and 406b to the phone numbers in Table 1 to determine a pharmacy identifier associated with "Your Pharmacy".

In another example, the extracted text data may include a pharmacy name, such as pharmacy name 404b presented by pharmacy receipt 400b. The prescription system 110 can compare the pharmacy name 404b to the pharmacy names in Table 1 to determine a pharmacy identifier associated with "Your Pharmacy".

In at least one embodiment, extracting the pharmacy identifier may include extracting graphical elements in the image and processing the graphical elements. For example, the prescription system 110 may extract a barcode, such as the barcode 416 in the prescription document 400a. In another example, the prescription system 110 may extract a logo associated with the pharmacy, such as the pharmacy logo 414a in the prescription document 400a. The prescription system 110 can then process the extracted graphical elements to determine the pharmacy identifier. For example, prescription system 110 may read the lines of a barcode to determine the pharmacy identifier. In another example, the prescription system 110 may compare a pharmacy logo to a list of pharmacy logos associated with particular pharmacies.

At act 330, the prescription system 110 selects, based on the pharmacy identifier, at least one parsing method for parsing prescription documents issued by the pharmacy identified by the pharmacy identifier. As will be described in further detail below, a parsing method can be applied to determine a medical product identifier and/or a prescription identifier. Accordingly, various parsing methods can be stored in the storage 114 or another data store and can be linked to the one or more pharmacy identifiers so that the right parsing method can be used once the pharmacy identifier is found.

Prescription documents may vary in format, depending on the issuing pharmacy. For example, as shown in FIGS. 4A and 4B, prescription document 400a has a different format than prescription document 400b. In particular, medical product information 408a of prescription document 400a is located in a different location than medical product information 408b of prescription document 400b. Moreover, prescription number 412a is located in a different location than prescription number 412b. Furthermore, prescription number 412a includes the prefix "Rx, whereas prescription number 412b does not include a prefix.

The prescription system 110 can select a parsing method that is appropriate for the particular format of the prescription document issued by the pharmacy corresponding to the pharmacy identifier. For example, the selected parsing method may be specific to the position and format of particular information on prescription documents issued by a particular pharmacy. In at least one embodiment, the prescription system 110 can access predetermined pharmacy data in order to determine the appropriate parsing method. For example, the prescription system 110 can determine from Table 1, based on a pharmacy identifier for "Your Pharmacy", that the prescription document type is "Type A". The prescription system 110 can then determine a parsing method for "Type A" prescription documents.

At act 340, the prescription system 110 applies the selected parsing method to the image data to determine a medical product identifier. The medical product identifier can be any suitable identifier for identifying the medical product dispensed by the pharmacy. In some countries, legislation or regulation requires a unique identifier to be assigned to every medication intended for human use. For example, in Canada, drugs are required to have a Drug Identification Number (DIN), and natural health products are required to have a Natural Product Number (NPN). In the United States, every medication is assigned a National Drug Code (NDC) by the Food and Drug Administration (FDA). In some cases, the medical product identifier can include a NDC, a DIN, and/or a NPN. In some cases, the medical product identifier can include a brand name, a generic name, and/or a chemical name.

Different parsing methods, when applied by prescription system 110 to image data, can determine the medical product identifier in different ways. Reference is now made to FIG. 5, which shows a flowchart illustrating an example embodiment of a method 500 for applying a parsing method to determine a medical product identifier, which may be implemented as act 340 of method 300.

At act 510, the prescription system 110 determines, based on the pharmacy identifier, at least one format associated with the medical product identifier. The format associated with the medical product identifier may identify the format of particular information on a prescription document. For example, for prescription document 400a, the parsing method may identify the presence of the prefix "NDC" in medical product information 408a. The determined format can differ depending on the pharmacy and the prescription documents issued by that pharmacy.

At act 520, the prescription system 110 determines, based on the pharmacy identifier, at least one location in the image data associated with the medical product identifier. The location associated with the medical product identifier may identify the location of particular information on a prescription document. For example, for prescription document 400a, the parsing method may identify the location of medical product information 408a. The determined location can differ depending on the pharmacy and the prescription documents issued by that pharmacy.

At act 530, the prescription system 110 extracts, from the image data, at the at least one determined location, image data associated with the medical product identifier. For example, the parsing method can extract the associated image data at the location corresponding to medical product information 408a in prescription document 400a.

At act 540, the prescription system 110 processes the associated image data, based on the at least one format, to determine the medical product identifier. In at least one embodiment, processing the associated image data can include removing at least some of the image data. For example, the extracted image data may correspond to medical product information 408a in prescription document 400a. The prescription system 110 can use an OCR method to convert the extracted image data into text data, such as "NDC 0173-0682-24". The prescription system 110 can remove the "NDC" prefix to determine the medical product identifier, "0173-0682-24".

In at least one embodiment, the parsing method may not extract a subset of image data from the captured image data. In such cases, the parsing method may be applied to text data to determine the medical product identifier. In such cases, the image processing method may identify a location within the text data to extract data and a format to process the extracted data. For example, the parsing method may be applied to text data extracted from the image data at act 320 during extraction of the pharmacy identifier. In some embodiments, the parsing method may identify a location associated with a particular text string, such as a prefix, such as "Rx" or "NDC". In some embodiments, the parsing method may identify a location associated with a text string having a particular format, such as three groups of numbers totaling 10 digits.

In at least one embodiment, the prescription system 110 can use an OCR method to extract all text data from the image data. For example, prescription system 110 may extract all of the text from image data of prescription document 400a. The extracted text data may include "Feb. 5, 2019, (703) 571-1001 Your Pharmacy (1) Ventolin 90 mcg NDC 0173-0682-24 Your Name 123 Address Ave Cost: $30.46 My Town Official Prescription document Rx 1886456". It will be appreciated that, although the text data is formatted left to right, top to bottom, the text data may be formatted in any manner. The prescription system 110 can then apply the parsing method to determine the medical product identifier, "0173-0682-24".

In at least one embodiment, the prescription system 110 can apply the selected parsing method to the image data to determine a prescription identifier. The prescription identifier can be any suitable identifier for identifying the prescription associated with the prescription document. In some cases, the prescription identifier can include a prescription (Rx) number. A prescription number may be a unique number assigned by a pharmacy that is associated with a specific fill/refill of a medication. For example, prescription system 110 can apply the parsing method to image data of prescription document 400a to determine prescription number 412a. In at least one embodiment, the prescription system can apply the selected parsing method to a QR code or a barcode to determine a prescription identifier.

In at least one embodiment, the prescription system 110 can apply the selected parsing method to the prescription image data to determine other information. For example, the prescription system 110 may determine one or more of the date of the prescription, the amount of the medical product prescribed, and the number of refills prescribed. In at least one embodiment, the prescription system 110 can store the determined information. For example, the prescription system 110 can track various information to create a prescription inventory or a medical record. The prescription system 110 can also transmit the determined information to external servers 150. For example, the determined information can be shared with pharmacy server 150a or research server 150b. In another example, the prescription system 110 may determine at least one of the name or license number of the prescriber (e.g., the prescribing doctor, nurse, etc.), the name or license number of the pharmacist, and the cost of the medication (which may include a pharmacy fee, cost, or total). The prescription system 110 may also collect the patient's name, address, and/or phone number.

It will be appreciated that in at least one embodiment the parsing method can determine a prescription identifier or other information in a similar fashion as it determines the medical product identifier. For example, the parsing method can determine various locations and formats, and perform various extraction and processing.

In at least one embodiment, the prescription system 110 can determine a medical product identifier, pharmacy identifier, and/or prescription identifier by other means. That is, referring back to act 230 in FIG. 2, the prescription system 110 can determine a medical product identifier, a pharmacy identifier, and/or prescription identifier by methods other than method 300. In some cases, the prescription system 110 may receive the identifier from the patient via the computing device 120. For example, as shown in FIG. 5A, the patient may select button 504 to manually enter a medical product identifier, such as DIN, which can be transmitted to the prescription system 110.

In at least one embodiment, the prescription system 110 can prompt a user to confirm that the medical product identifier, pharmacy identifier, and/or prescription identifier determined by the prescription system 110 is correct. For example, the prescription system 110 may request the user to submit corrections to the determined medical product identifier, pharmacy identifier, and/or prescription identifier via the computing device 120. The prescription system 110 can store the determined identifiers and corrections in association with the parsing methods and image data used to determine the identifiers. The prescription system 110 may modify or adjust the parsing methods based on the stored data to improve the accuracy of the parsing methods.

In at least one embodiment, the prescription system 110 may be unable to select a parsing method based on a pharmacy identifier. For example, the prescription system 110 may fail to identify a pharmacy identifier at act 310. Alternatively, the prescription system 110 may be unable to identify a parsing method associated with a pharmacy identifier identified at act 310. For example, the prescription system 110 be unable to determine a prescription document format type for the identified pharmacy because of incomplete or missing pharmacy data stored by the prescription system 110.

In these cases, the prescription system 110 can apply one or more non-specific parsing methods to determine the medical product identifier, pharmacy identifier, and/or prescription identifier. The prescription system 110 can then verify the identifiers determined by the non-specific parsing methods based on one or more user inputs. For example, as noted above, the prescription system 110 may request a user to submit corrections via the computing device 120.

The prescription system 110 can then store the corrected identifiers and any associated data. The prescription system 110 may use the stored data to adjust or modify the parsing methods. The prescription system 110 may also use the stored data to update the data maintained by the prescription system 110. For example, the prescription system 110 may store a prescription document format type in association with a parsing method or a pharmacy identifier so that the same parsing method can be used during subsequent processing of prescription documents of a particular format type or associated with a particular pharmacy.

In at least one embodiment, the prescription system 110 may determine other data in addition or alternate to determining the medical product identifiers, pharmacy identifiers, and/or prescription identifiers. For example, the prescription system 110 may determine a physiological measurement printed on the prescription document (e.g., when the prescription document is a lab report). For instance, the prescription system 110 may determine a pharmacy identifier (e.g. a lab identifier) associated with the prescription document, select a parsing method based on that pharmacy identifier, and apply the parsing method to determine the physiological measurement.

The prescription system 110 can use medical product identifiers, pharmacy identifiers, and/or prescription identifiers in various ways. Referring back to FIG. 2, at act 240, the prescription system 110 can provide various personalized services. For example, the prescription system 110 can provide patients via computing devices 120 with instructions, notifications, and various other information based on medical product, pharmacy, and/or prescription identifiers. The prescription system 110 can allow patients to reorder medication and submit data to various parties via computing devices 120, including pharmacies and/or research organizations, based on medical product, pharmacy, and/or prescription identifiers. Prescription system 110 can provide such functionality without reliance on personal information from patients or third parties, through the use of the medical product, pharmacy, and/or prescription identifiers. To illustrate these methods of operating the prescription system 110, reference will now be made to FIGS. 7A to 7E.

In at least one embodiment, the prescription system 110 can determine, based on a medical product identifier, at least one instruction for administering the medical product associated with the medical product identifier. The prescription system 110 can transmit the at least one instruction to the computing device 120. In some cases, this may include transmitting a video file, an audio file, and/or a text file. For example, the prescription system 110 can transmit instructional videos, instructional images, or instructional text to the computing device 120 to inform the patient on how to administer a particular medication. In some cases, the prescription system 110 may transmit a link, reference, or location to the at least one instruction. Patients can also be provided with medical product monographs, educational videos, and resources specific to that medication. Patients may also be given information regarding side effects or adverse medical product interactions.

Figures 7A, 7B:
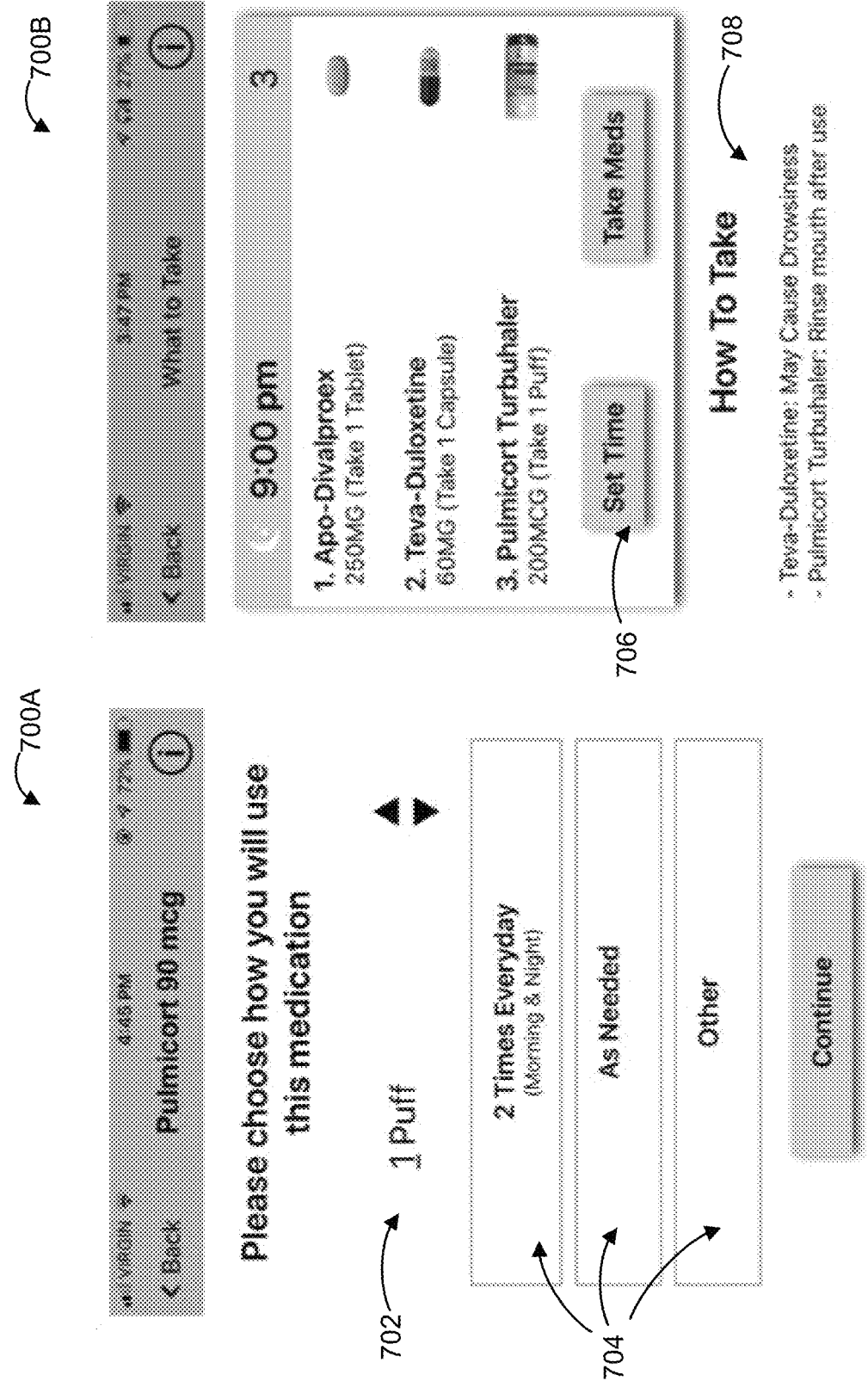
FIGS. 7A to 7E are illustrations of example embodiments of user interfaces that can be used to facilitate the operation of the prescription system disclosed herein.
Figures 7C, 7D:
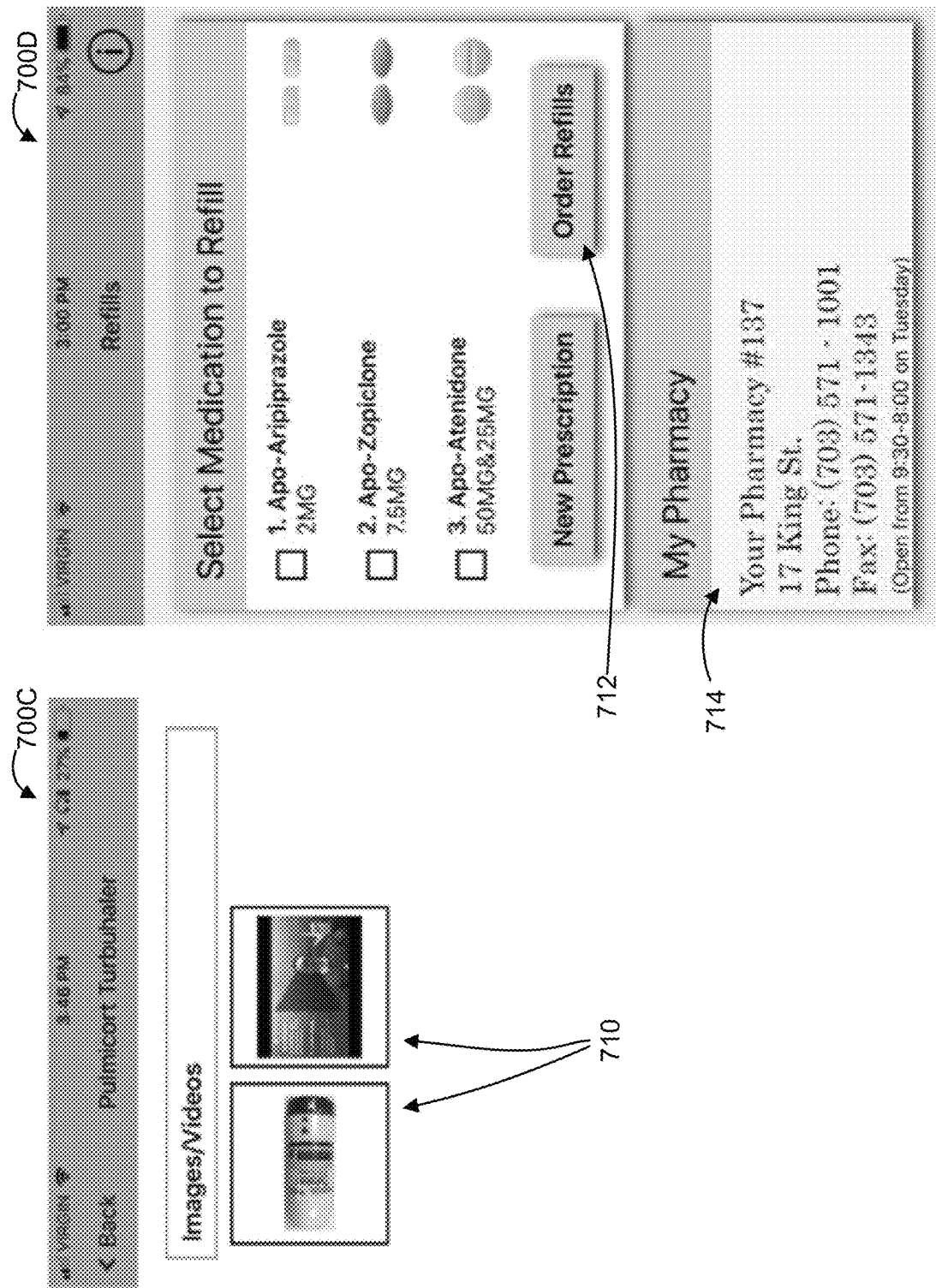

For example, FIGS. 7B and 7C show example user interfaces 700B and 700C, which show examples of instructions that can be displayed at the computing device 120. User interface 700B shows example text instructions 708 for administering the medications "Teva-Duloxetine" and "Pulmicort Turbuhaler". User interface 700C shows example image and video instructions 710 for the medical product "Pulmicort Turbuhaler".

In at least one embodiment, the prescription system 110 can determine the at least one instruction based on predetermined medical product data. Table 2 illustrates an example of medical product data which can be accessed by the prescription system 110. The medical product data can be stored, for example, at storage 114 and/or storage 130.

TABLE 2

| Example Medical Product Data | | |
|---|---|---|
| NDC | 0173-0682-24 | 0186-0917-65 |
| Brand Name | Ventolin | Pulmicort |
| Generic Name | Salbutamol | Budesonide |
| Dose | 90 mcg | 90 mcg |
| Unit | Puff(s) | Puff(s) |
| Direction | Four Times a Day | Morning & Night |
| How to Take | Shake Well | Rinse Mouth After |
| Video | http://www . . . | http://www . . . |
| Metabolism | None | none |

In at least one embodiment, the prescription system 110 causes a processor of the computing device 120 to generate a notification for alerting a user to administer the medical product. For example, the prescription system 110 can determine dosage regiments for a medical product and cause computing device 120 to generate a notification, at the appropriate time, reminding a patient to take the medical product.

In at least one embodiment, the prescription system 110 can receive a confirmation from the computing device 120 indicating that the patient took the medical product. In such embodiments, the prescription system 110 may cause the computing device 120 to repeatedly generate notifications until the confirmation is received. In at least one embodiment, the prescription system 110 may generate an alert to a third party indicating the patient's failure to confirm taking the medical product. In at least one embodiment, the prescription system 110 may generate periodic reports indicating the patient's failure to confirm taking the medical product.

In at least one embodiment, the patient can customize the dosage timings for administering the medical product. For example, the prescription system 110 can provide the patient with common or suggested dosage regiments, which can then be modified by the patient. FIG. 7A shows an example user interface 700A that can be used by a patient for modifying a dosage regiment. A patient can modify the dosage of the medication "Pulmicort" using element 702 and the dosage time using element 704 of user interface 700A.

In at least one embodiment, the prescription system 110 can cause a processor of the computing device 120 to generate an alert for warning a patient. For example, the prescription system 110 may receive a warning or medical product recall from an external server 150, which may be associated with a patient advocacy group, health organization, medical product manufacturer, or government organization. The prescription system 110 can determine the medical product identifier associated with the medical product and transmit an alert to patients associated with the medical product identifier via computing devices 120.

In at least one embodiment, the prescription system 110 can determine, based on the medical product identifier, a plurality of other computing devices associated with the medical product associated with the medical product identifier. The prescription system 110 can then transmit the at least one instruction to the computing device and the plurality of other computing devices. For example, the prescription system 110 can enable the operation of medication specific patient support programs. After identifying patients who are taking particular medications, the prescription system 110 can periodically send motivational messages, educational articles, or other information to the patients via the computing devices 120. In at least one embodiment, the prescription system 110 can communicate with the patient via computing device 120 to improve the patient safety and satisfaction. For example, the patient can be prompted to ask for specific side effects or patients may share their physiological readings to have them monitored. In at least one embodiment, the prescription system 110 can connect patients to resources made available by the medical product manufacturer, such as a patient telephone help line. For example, in some embodiments, the prescription system 110 can provide user interfaces with a custom layout, appearance, or functionality based on the medication.

In at least one embodiment, the prescription system 110 can receive, from the computing device 120, a user request for refilling a prescription associated with the prescription document. The prescription system 110 can locate, based on the pharmacy identifier, a pharmacy server 150a associated with the pharmacy associated with issuing the prescription document. The prescription system 110 can then transmit a server request for refilling the prescription to the pharmacy server 150a where the server request includes the medical product identifier. For example, FIG. 7D shows an example user interface 700D for refiling a prescription. A patient can press button 712 on user interface 700D via the computing device 120 to order a refill of their prescription. For example, once the computing device 120 receives user input that the user has pressed the button 712 to request a refill, the computing device 120 can then send the refill request to the appropriate pharmacy server 150a.

In at least one embodiment, the pharmacy server 150a may include an email client, which can accept emails from the prescription system 110. Accordingly, the prescription system 110 may transmit the server request for fulfilling the prescription in the form of an email. In at least one embodiment, the pharmacy server 150a may include a pharmacy software, which can accept the server request from the prescription system 110. In such embodiments, the prescription system 110 may format the server request to comply with the pharmacy software.

In at least one embodiment, the prescription system 110 can transmit other information with the medical product identifier to the pharmacy server 150a. For example, the prescription system 110 may transmit information related to recalls, patient support programs, news or developments, counselling points, medical product interactions, educational courses, common doses, black box warnings, or other medical product information.

In at least one embodiment, the prescription system 110 can determine the turnaround time for refiling the prescription and whether the pharmacy allows for deliveries.

Figure 7E:
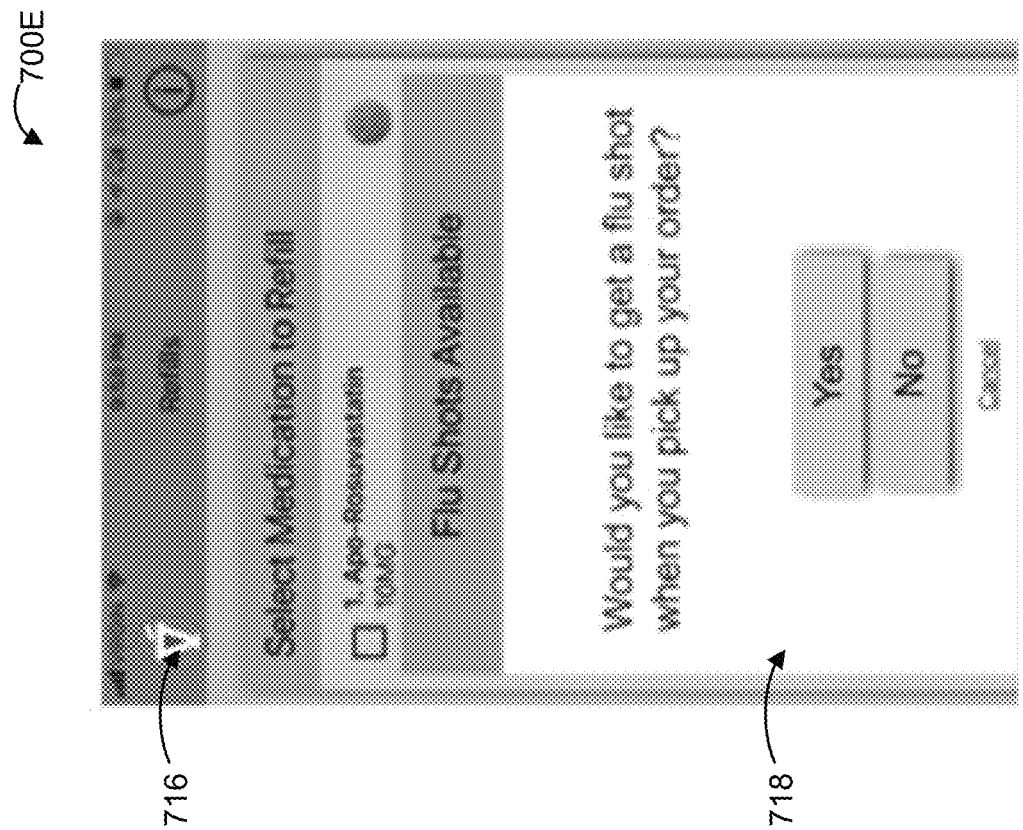

In at least some embodiments, the prescription system 110 can generate custom user interfaces by adjusting at least one of the appearance and functionality of the user interface based on the pharmacy identifier. For example, the prescription system 110 can generate a custom user interface at the computing device 120 based on desired settings providing by the pharmacy associated with the pharmacy identifier. For example, FIG. 7D shows an example user interface 700D that is customized based on the pharmacy. User interface 700D includes various information that is specific to the pharmacy in element 714, such as the name, address, phone number, fax number, and hours of operation. In another example, FIG. 7E shows an example user interface 700E that is customized based on the pharmacy. User interface 700E includes a customized logo 716 and a customized message 718, which informs users that flu shots are available at the pharmacy. Other examples of possible custom user interfaces can include various custom layouts and color schemes. For example, in at least one embodiment, the custom user interfaces can be designed to match the branding of the pharmacy.

In at least one embodiment the prescription system 110 can adjust appearance or functionality based on predetermined pharmacy data. Table 3 illustrates an example of pharmacy data which can be accessed by the prescription system 110. The pharmacy data can be stored, for example, at storage 114 and/or storage 130.

TABLE 3

Example Pharmacy Data

| | | |
|---|---|---|
| Pharmacy Phone Number | (202) 456-1111 | (703) 571-1001 |
| Pharmacy Name | Your Pharmacy #102 | Your Pharmacy #137 |
| Pharmacy Fax | (202) 456-1311 | (703) 571-1343 |
| Address | 1563 Queen St. | 17 King St. |
| Weekday Hours | 10:00-6:00 | 9:30-8:00 |
| Custom Logo | Vina.jpg | No |
| Allow Deliveries | Yes | No |
| Flu Shots | No | FluConsent4 |

In at least one embodiment, the prescription system 110 can transmit a request to the computing device 120 for at least one physiological measurement of a patient that is receiving administration of the medical product. The prescription system 110 can receive, from the computing device 120, the at least one physiological measurement. For example, the computing device 120 may have a sensor that can sense the physiological data or the patient can input the physiological data which may include, but it not limited to, blood pressure, temperature, heart rate, weight, and blood oxygenation. The prescription system 110 can then store, in a memory, the at least one physiological measurement with the medical product identifier. For example, the prescription system 110 can request, receive and store the number of doses, patient mood, amount of sleep, blood pressure, blood sugar level, etc. In at least one embodiment, the stored physiological measurement can be transmitted to other parties, such as through external servers 150. For example, the information may be shared with the pharmacy, prescribers, patient support programs or researchers. Other information can also be stored or shared, such as adherence rate and a list of medications. In at least one embodiment, the prescription system 110 can obtain consent from a patient prior to sharing the information.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A computer implemented method for determining a medical product dispensed by a pharmacy, the method comprising operating a processor to:
   receive, from a computing device, an image data depicting at least a portion of a prescription document issued by the pharmacy;
   extract, from the image data, a pharmacy identifier for identifying the pharmacy associated with issuing the prescription document;
   select, based on the pharmacy identifier, at least one parsing method for parsing prescription documents issued by the pharmacy identified by the pharmacy identifier; and
   apply the selected parsing method to the image data to determine a medical product identifier for identifying the medical product dispensed by the pharmacy.

2. The method of claim 1, wherein applying the selected parsing method to the image data comprises:
   determining, based on the pharmacy identifier, at least one format associated with the medical product identifier;
   determining, based on the pharmacy identifier, at least one location in the image data associated with the medical product identifier;
   extracting, from the image data, at the at least one determined location, image data associated with the medical product identifier; and
   processing the associated image data, based on the at least one format, to determine the medical product identifier.

3. The method of claim 2, wherein processing the associated image data comprises removing at least some of the associated image data based on the at least one format.

4. The method of claim 1, wherein extracting the pharmacy identifier comprises extracting, from the image data, a telephone number associated with the pharmacy.

5. The method of claim 1, wherein:
   extracting the pharmacy identifier comprises: extracting text data from the image data, and extracting the pharmacy identifier from the text data; and
   applying the selected parsing method to the image comprises: applying the selected parsing method to the text data to determine the medical product identifier.

6. The method of claim 1, further comprising operating the processor to:
   determine, based on the medical product identifier, at least one instruction for administering the medical product associated with the medical product identifier; and
   transmit the at least one instruction to the computing device.

7. The method of claim 6, further comprising operating the processor to:
   determine, based on the medical product identifier, a plurality of other computing devices associated with the medical product associated with the medical product identifier; and
   transmit the at least one instruction to the computing device and the plurality of other computing devices.

8. The method of claim 6, wherein receipt of the at least one instruction causes the processor of the computing device to generate a notification for alerting a user to administer the medical product.

9. The method of claim 1, further comprising operating the processor to:
   receive, from the computing device, a user request for refilling a prescription associated with the prescription document;
   locate, based on the pharmacy identifier, a pharmacy server associated with the pharmacy associated with issuing the prescription document;
   generate a server request for refilling the prescription; and
   transmit the server request for refilling the prescription to the pharmacy server, the server request including the medical product identifier.

10. The method of claim 1, further comprising operating the processor to:
    transmit a request for at least one physiological measurement of a user associated with administration of the medical product to the computing device;
    receive, from the computing device, the at least one physiological measurement; and
    store, in a memory, the at least one physiological measurement with the medical product identifier.

11. A system for determining a medical product dispensed by a pharmacy, the system comprising:
    a memory for storing a plurality of parsing methods, each parsing method for parsing prescription documents issued by a particular pharmacy; and
    a processor operable to:
      receive, from a computing device, image data depicting at least a portion of a prescription document issued by the pharmacy;
      extract, from the image data, a pharmacy identifier for identifying the pharmacy associated with issuing the prescription document;
      select, based on the pharmacy identifier, at least one parsing method stored in the memory for parsing prescription documents issued by the pharmacy identified by the pharmacy identifier; and
      apply the selected parsing method to the image data to determine a medical product identifier for identifying the medical product dispensed by the pharmacy.

12. The system of claim 11, wherein applying the selected parsing method to the image data comprises:
    determining, based on the pharmacy identifier, at least one format associated with the medical product identifier;
    determining, based on the pharmacy identifier, at least one location in the image associated with the medical product identifier;
    extracting, from the image data, at the at least one determined location, image data associated with the medical product identifier; and processing the associated image data, based on the at least one format, to determine the medical product identifier.

13. The system of claim 12, wherein processing the associated image data to determine the medical product identifier comprises removing at least some of the image data based on the at least one format.

14. The system of claim 11, wherein extracting the pharmacy identifier comprises extracting, from the image data, a telephone number associated with the pharmacy.

15. The system of claim 11, wherein:
extracting the pharmacy identifier comprises: extracting text data from the image data, and extracting the pharmacy identifier from the text data; and
applying the selected parsing method to the image comprises: applying the selected parsing method to the text data to determine the medical product identifier.

16. The system of claim 11, wherein the processor is further operable to:
determine, based on the medical product identifier, at least one instruction for administering the medical product associated with the medical product identifier; and
transmit the at least one instruction to the computing device.

17. The system of claim 16, wherein the processor is further operable to:
determine, based on the medical product identifier, a plurality of other computing devices associated with the medical product associated with the medical product identifier; and
transmit the at least one instruction to the computing device and the plurality of other computing devices.

18. The system of claim 16, wherein receipt of the at least one instruction causes the processor of the computing device to generate a notification for alerting a user to administer the medical product.

19. The system of claim 11, wherein the processor is further operable to:
receive, from the computing device, a user request for refilling a prescription associated with the prescription document;
locate, based on the pharmacy identifier, a pharmacy server associated with the pharmacy associated with issuing the prescription document;
generate a server request for refilling the prescription; and
transmit the server request for refilling the prescription to the pharmacy server, the server request including the medical product identifier.

20. The system of claim 11, wherein the processor is further operable to:
transmit a request for at least one physiological measurement of a user associated with administration of the medical product to the computing device;
receive, from the computing device, the at least one physiological measurement; and
store, in the memory, the at least one physiological measurement with the medical product identifier.

* * * * *